United States Patent [19]
Bar-Or et al.

[11] Patent Number: 5,727,949
[45] Date of Patent: Mar. 17, 1998

[54] REFERENCE DEVICE FOR PROGNOSING SKIN LESIONS

[76] Inventors: David Bar-Or; Raphael Bar-Or, both of 900 E. Oxford La., Englewood, Colo. 80110

[21] Appl. No.: 738,986

[22] Filed: Oct. 24, 1996

[51] Int. Cl.$^6$ .......................... G09B 23/28; G09B 25/00; G09F 11/04
[52] U.S. Cl. .................. 434/267; 434/262; 434/402; 434/404; 434/405; 40/495; 40/491
[58] Field of Search ................... 434/262, 267, 434/402, 404, 405, 219; 40/495, 491

[56] References Cited

U.S. PATENT DOCUMENTS

| | | | |
|---|---|---|---|
| 1,988,634 | 1/1935 | Stonecypher | 434/262 |
| 3,186,111 | 6/1965 | Lawlor | 434/262 |
| 3,571,947 | 3/1971 | Maddison | 434/262 |
| 5,505,623 | 4/1996 | Chernack et al. | 434/402 X |

*Primary Examiner*—Jeffrey A. Smith
*Attorney, Agent, or Firm*—Timothy J. Martin; Michael R. Henson

[57] ABSTRACT

A reference device for use in indicating prognosis of a physical condition based upon selected diagnostic characteristics of the physical condition. The reference device may include a first panel member having first selected diagnostic characteristics of the physical condition distributed thereon, and a second panel member including second selected diagnostic characteristics of the physical condition distributed thereon as well as prognosis indicators associated with the second selected diagnostic characteristics. The first and second panels are mounted for relative movement whereby a selected one of the first selected diagnostic characteristics may be paired with a selected one of the second diagnostic characteristics and a determinable prognosis is revealed corresponding the specific paired characteristics. The reference device is particularly useful for prognosing melanoma based upon diagnostic characteristics of a skin lesion.

30 Claims, 9 Drawing Sheets

1

REFERENCE DEVICE FOR PROGNOSING SKIN LESIONS

FIELD OF INVENTION

The present invention is generally directed to a reference device for use in indicating prognosis of a physical condition based upon selected diagnostic characteristics of the physical condition. More particularly, the present invention is concerned with such a reference device which may be used for prognosing melanoma based upon diagnostic characteristics of a skin lesion.

BACKGROUND OF THE INVENTION

For years, cancer has been one of the leading causes of death in the United States. While the precise causes of many types of cancer are unknown, there can be little doubt that certain activities, such as cigarette smoking, is directly related to cancer of the lung, oral cavity and larynx. Despite society's long time awareness of the proliferation of cancer, the medical community continues to struggle for cures and a greater understanding of its origins.

Cancer is the commonly recognized name for a malignant neoplasm or tumor. Neoplasm is a pathological lesion characterized by the progressive or uncontrolled proliferation of cells. Neoplastic growths are generally described as either benign or malignant types, although in certain instances the distinction is somewhat unclear. The most important differentiating feature between a benign and malignant neoplasm is that a malignant tumor will invade surrounding structures and metastasize, or spread, to different sites, whereas a benign tumor will not. Benign tumors grow slowly, remain localized, and generally can be successfully and finally removed if treated properly. Malignant tumors, on the other hand, tend to grow rapidly, spread throughout the body and recur if removed. Those malignant tumors which are derived from epofilia cells and tissues, such as skin, are referred to as carcinomas, whereas those which arise from mesenchymal cells, such as bone and muscle, are referred to as sarcomas.

Regardless of the particular type of tumor encountered, early detection can be critical from a medical standpoint so that benign tumors can be effectively treated before they evolve into a life threatening disease. Where skin lesions in particular are concerned, early detection can usually be made by either a doctor or an alert patient to make an early prognosis of the likelihood that the skin lesion may develop into a malignant tumor. For example, a widely used technique for assessing such a likelihood is to perform a preliminary diagnosis of the skin abnormality based on various appearance characteristics, such as a symmetry, border, coloration, diameter and enlargement. Understandably, there can be numerous variations of these five characteristics for any given skin condition. For example, a growth can have a symmetry which ranges from none to high, a color ranging from homogeneous to highly varied, a border with an appearance ranging from either round to irregular and ill defined, and a diameter which can range from very small to greater than 12 mm. Depending on the particular combination on these characteristics which a skin growth possesses, a prognosis can be made as to the likelihood that the condition is cancerous.

With this in mind, then, it would be desirous for doctors and patients to have a ready reference guide so that a preliminary prognosis of a skin condition can be made based on a diagnosis of these various characteristics. Most patients prior to visiting with a medical practitioner, are unaware of the early signs of melanoma growths. Accordingly, such a reference guide may be invaluable in the early detection and treatment of such growths. Moreover, with the hectic schedule of many medical practitioners today, such a reference guide could save both time and money in the treatment of these skin conditions. The present invention is directed to meeting these needs, among others.

SUMMARY OF INVENTION

It is an object of the present invention to provide a new and useful reference device that is adapted for use in determining prognosis of a physical condition.

Another object of the present invention is to provide a new and useful reference device wherein such a prognosis can be determined based upon a variety of selected diagnostic characteristics of the physical condition.

A further object of the present invention is to provide a reference device which is particularly adapted at assessing the risk that a given skin condition is melanoma.

Yet another object of the present invention is to provide a new and useful reference device which is relatively inexpensive to manufacture and which can be easily operated by either a patient or a physician to prognosticate the physical condition.

The present invention is directed to a reference device for indicating prognosis of a physical condition based on selected diagnostic characteristics of the physical condition. In its broadest form, the present invention comprises first and second panel members which are mounted for relative movement with one another. The first panel member has a first panel member surface and this first panel member surface includes a plurality of first selected diagnostic characteristics of the physical condition distributed thereon in a first array which is defined in that adjacent ones of the first selected diagnostic characteristics are spaced apart relative to one another from a first reference point on the first panel member surface. The first panel member surface also includes a viewing window associated with each of the plurality of first selected diagnostic characteristics. The second panel member has a second panel member surface which includes a plurality of second selected diagnostic characteristics of the physical condition and these second selected diagnostic characteristics are distributed thereon in a second array which is defined in that adjacent ones of these characteristics are spaced apart relative to a second reference point on the second panel member surface. The second panel member further includes a plurality of prognosis indicators associated with each of the second selected diagnostic characteristics.

The second panel member is movable relative to the first panel member whereby selected ones of the first and second selected diagnostic characteristics may be paired to define a specific combination of diagnostic characteristics so that the viewing window associated with the selected one of the first selected diagnostic characteristics automatically registers with one of the plurality of prognosis indicators associated with the selected one of the second diagnostic characteristics, thereby to reveal a determinable prognosis indicator corresponding to the specific combination of diagnostic characteristics.

The second panel member may be slidable relative to the first panel member, but it is preferred that the panel members are operative to rotate relative to one another about an axis of rotation passing through their reference points. Where the panel members are rotatable relative to one another, it is preferred that they each be configured as a dial with the first panel member having a smaller diameter than the second panel member. Moreover, the first and second selected diagnostic characteristics of the physical condition may be respectively distributed on the panel members as a circular arrangement about the first and second reference points.

The second panel member may include at least a first set of the prognosis indicators associated with each of the plurality of the second selected diagnostic characteristics. These first sets of prognosis indicators are arranged in a matrix that is defined by a plurality of radially aligned columns and a plurality of arcuate rows, with the prognosis indicators in each of the rows positioned at a common radial distance from the second reference point. With this orientation, the viewing windows are located at a selected radial distance from the second reference point so that each of the viewing windows is positioned to sequentially pass over a row of prognosis indicators that is distributed at the selected radial distance from the second reference point. At least some of these viewing windows may be located at a common radial distance from the second reference point. It is preferred that the matrix formed by the first sets of prognosis indicators be centered about the second reference point.

The second panel member may also include a second set of prognosis indicators associated with each of the second selected diagnostic characteristics. With this construction, the first sets of prognosis indicators correspond to an enlarging growth of the physical condition and each of the second set of prognosis indicators corresponds to a stagnate growth of the physical condition. Here also, the first and second sets of prognosis indicators are arranged in a matrix as described above so that the viewing windows are positioned to sequentially pass over a row of prognosis indicators that is distributed at the selected radial distance from the second reference point.

Preferably, each of the first selected diagnostic characteristics and its associated viewing window occupies a delineated zone on the first panel member surface, with adjacent ones of these zones shaded differently thereby to emphasize presence and orientation of the zones. Likewise, each of the selected diagnostic characteristics and its associated prognosis indicators occupies a delineated zone on the second panel member surface, with adjacent ones of these zones shaded differently to emphasize presence and orientation thereof.

The present invention is also directed to a reference device for prognosing melanoma based upon selected diagnostic characteristics of a skin lesion. As such, it is preferred that the first and second panel members have their respective panel member surfaces indelibly marked with the selected diagnostic characteristics of the skin lesion. It is also preferred that a plurality of melanoma prognosis indicators by indelibly marked on the second panel member surface. With this construction, the first and second panel members are rotatable whereby desired first and second selected diagnostic characteristics of the skin lesion may be paired to reveal a determinable melanoma prognosis indicator corresponding to the specific combination of diagnostic characteristics.

Preferably, each of the plurality of first selected diagnostic characteristic of the skin lesion is a first combination of appearance characteristics selected from a group consisting of asymmetry, color, border and diameter of the skin lesion. Similarly, each of the plurality of second diagnostic characteristics of the skin lesion is a second combination of appearance characteristics selected from this same group, with the second combination being different from the first combination. The asymmetry appearance characteristic may be selected from a group consisting of no asymmetry, moderate asymmetry and high asymmetry. The border appearance characteristics may be selected from a group consisting of round, irregular, or irregular and ill defined. The color appearance characteristic is selected from a group consisting of homogeneous, varied and highly varied. The diameter appearance characteristic is selected from a group consisting of less than 6 mm, between 6–12 mm, and greater than 12 mm. Moreover, each of the plurality of melanoma prognosis indicators may be selected from a group consisting of low risk, moderate risk, high risk and very high risk.

In another embodiment of the present invention, the reference device incorporates three panel members for indicating prognosis of a physical condition based upon various selected diagnostic characteristics. With this embodiment, the first and second panel members are constructed similarly to that discussed above, with the exception that the second panel member also includes a viewing window associated with each of the plurality of second selected diagnostic characteristics. In addition, the third panel member, and not the second panel member, is provided with the plurality of prognosis indicators and these prognosis indicators are distributed on a third panel member surface in a graphic array relative to a third central reference point on the third panel member surface. The first, second and third panel members are mounted for relative movement with one another about an axis of rotation passing through their central reference points whereby selected ones of the first and second selected diagnostic characteristics may be paired to define a specific combination of diagnostic characteristic so that associated ones of the first and second panel member viewing windows register. The third panel member may thereafter be rotated so that one of the prognosis indicators may be viewed through the first and second viewing windows thereby to reveal a determinable prognosis indicator corresponding to the specific combination of diagnostic characteristics of the physical condition.

These and other objects of the present invention will become more readily appreciated and understood from a consideration of the following detailed description of the exemplary embodiments of the present invention when taken together with the accompanying drawings, in which:

BRIEF DESCRIPTION OF DRAWINGS

FIG. 12($b$) is a reduced top plan view of the reference device according to the third exemplary embodiment of the present invention with the first, second and third panel members registered to reveal a determinable prognosis indicator associated with a specific combination of diagnostic characteristics of an enlarging physical condition.

DETAILED DESCRIPTION OF THE EXEMPLARY EMBODIMENTS

The reference device of the present invention is adapted for use in indicating prognosis of a physical condition based upon selected diagnostic characteristics thereof. More specifically, the reference device is usable for prognosing melanoma based upon selected diagnostic characteristics of a patient's skin lesion. It is known in the medical community that skin lesions posses certain appearance characteristics and that a determinable risk that the skin lesion is melanoma, or cancerous may be prognosed based on these characteristics. The present invention, therefore, provides a ready reference guide which may be used either by a patient or the patient's doctor to easily and quickly ascertain a probable prognosis as to whether the skin lesion is benign or malignant. As the description of the exemplary embodiments proceeds, one of ordinary skill in the art would appreciate that although the reference device of the present invention is particularly described herein as a gauge for prognosing such skin lesions, it is contemplated that the prognosis of other physical conditions are also contemplated without departing from the inventive concepts herein.

Figure 1:
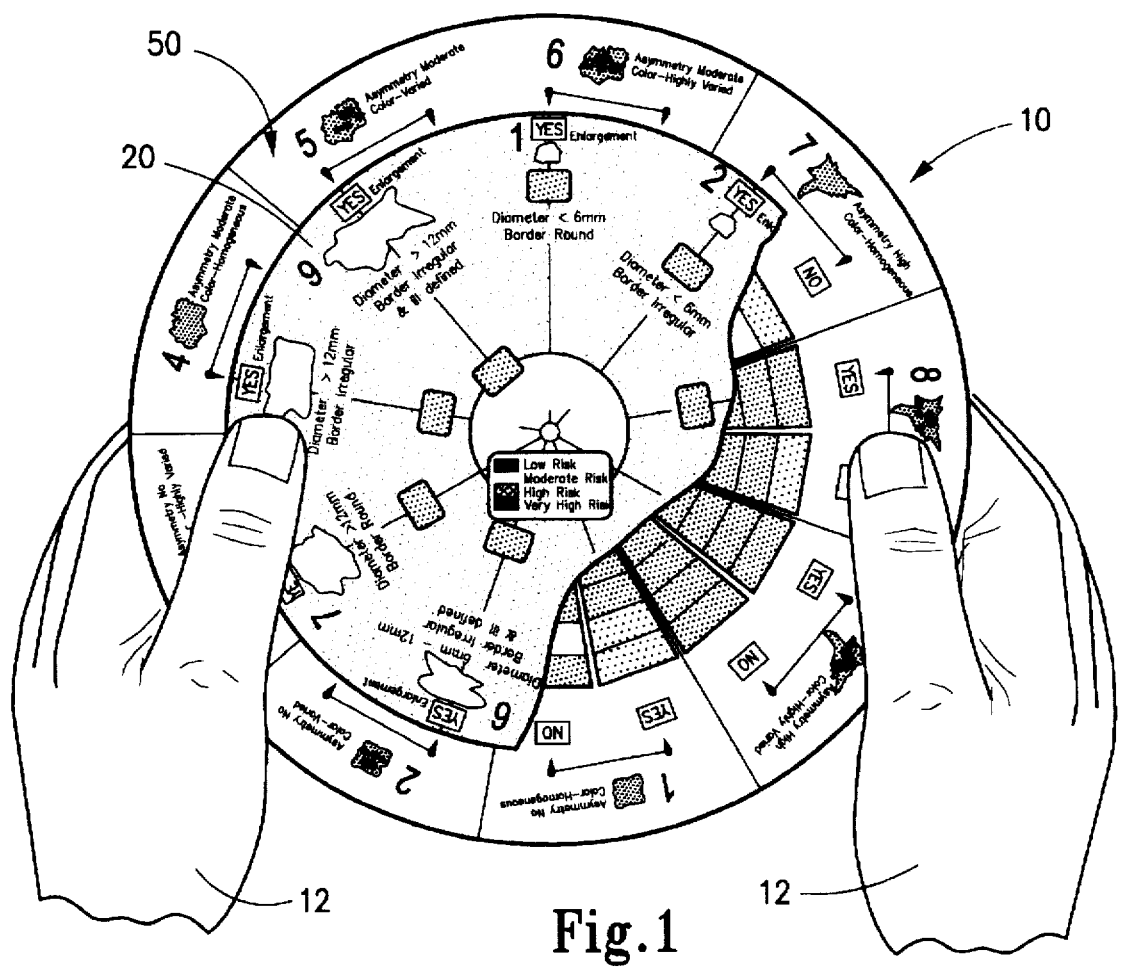
FIG. 1 is a top plan view, partially broken away, of a first exemplary embodiment of the reference device according to the present invention with a pair of human hands illustrated as holding and operating the reference device.
Figure 2:
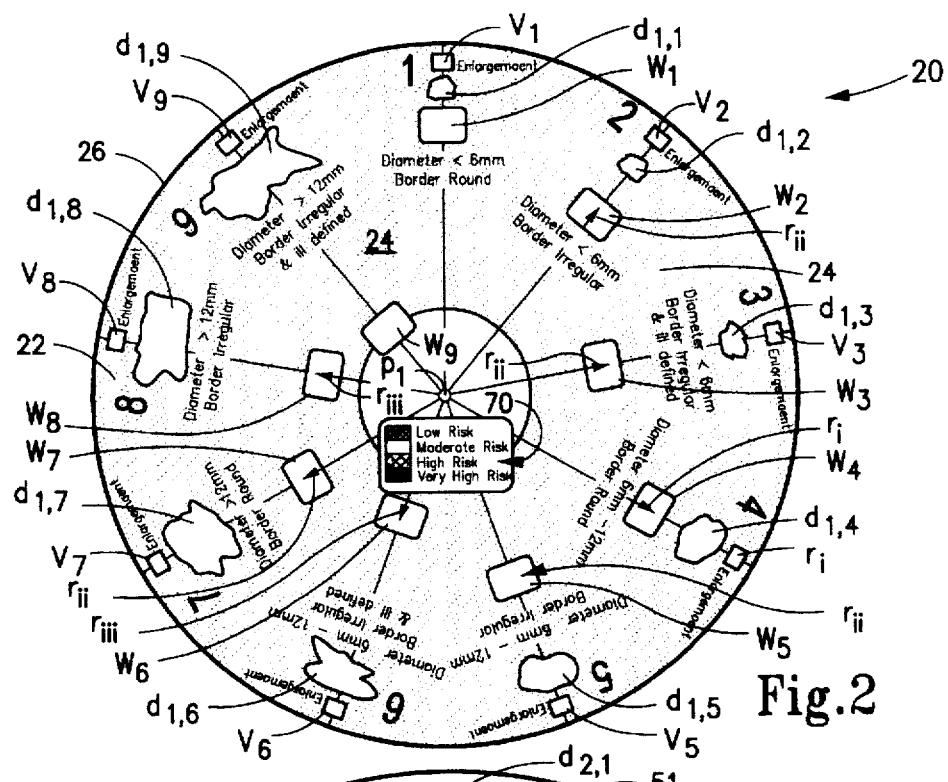
FIG. 2 is a top plan view showing the construction for the first (top) panel member which comprises a component part of the reference device according to the first exemplary embodiment of the present invention.
Figure 3:
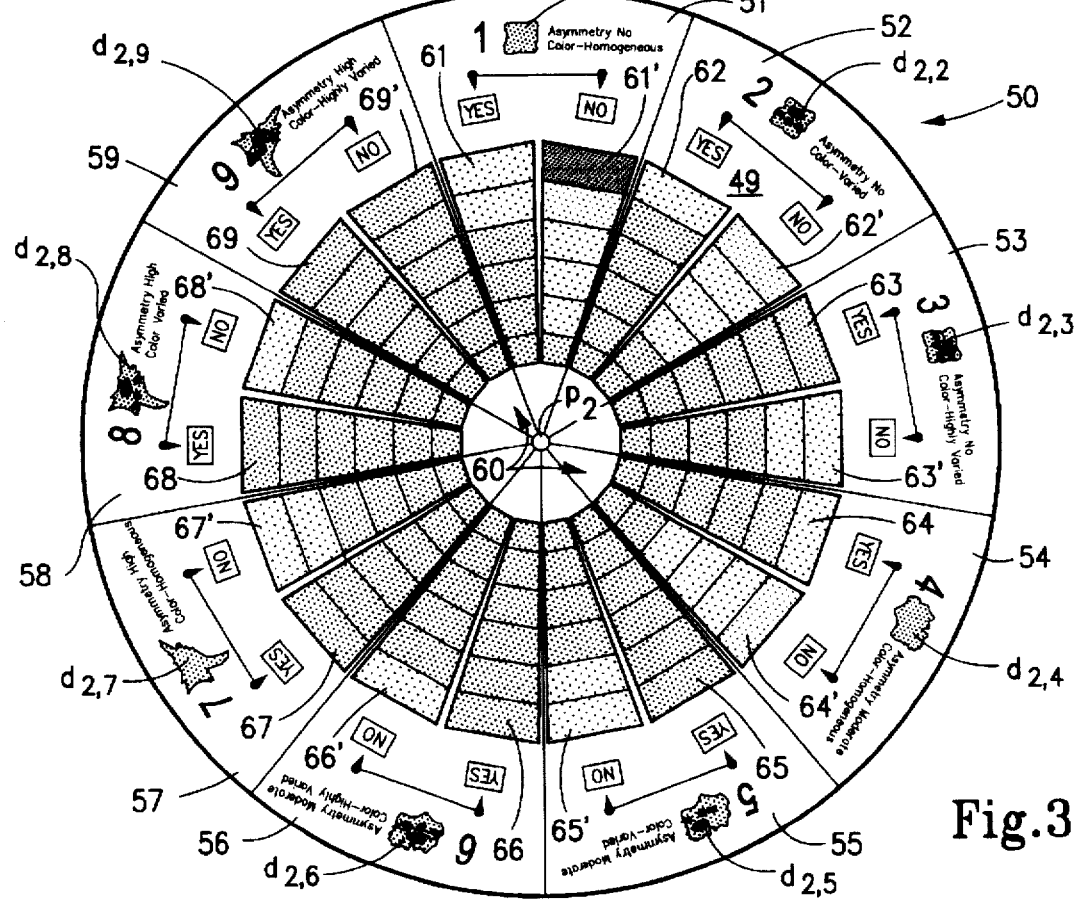
FIG. 3 is a top plan view showing the construction for the second (bottom) panel member which comprises a component part of the reference device according to the first exemplary embodiment of the present invention.

As generally introduced in FIGS. 1-3, a first exemplary embodiment of a reference device 10 of the present invention includes a first, or top, panel member 20 in the form of a dial and a second, or bottom, panel member 50 also in the form of a dial. First panel member 20 and second panel member 50 are fabricated from a stiff yet resilient material, such as plastic or paper, and are mounted for relative movement for ascertaining the prognosis of a physical condition, as described more thoroughly below. As specifically shown in FIG. 1, reference device 10 is sized and adapted to be grasped by a user's hands 12 so that the first and second panel members 20, 50 may be easily manipulated during use.

First panel member 20 is constructed as a circular dial and includes a plurality of first selected diagnostic characteristics of the physical condition, $d_{1,1}$ through $d_{1,9}$, distributed thereon in a first array 22. These first selected diagnostic characteristics $d_{1,1}$–$d_{1,9}$ are indelibly marked on a first panel member surface 24 of first panel member 20. First array 22 is defined in that adjacent ones of these first selected diagnostic characteristics $d_{1,1}$–$d_{1,9}$ are spaced apart relative to one another from a first central reference point "p1" on first panel member surface 24. More specifically, the first selected diagnostic characteristics $d_{1,1}$–$d_{1,9}$ are distributed as a circular arrangement about first central reference p1.

The first selected diagnostic characteristics $d_{1,1}$–$d_{1,9}$ are shown to be pictorial representations of certain characteristics of an encountered skin lesion. For example, these pictorial representations correspond to a first combination of appearance characteristics of the skin lesion, which first combination is denoted by both the border and the diameter of the lesion. To illustrate, then, a representative one of the first selected diagnostic characteristics $d_{1,1}$ is a pictorial representation of a skin lesion having a diameter of less than six millimeters (6 mm) and a border which is defined as round. Similarly, another representative one of the first selected diagnostic characteristics $d_{1,8}$ is a pictorial representation of a skin lesion having a diameter greater than twelve millimeters (12 mm) and a border which is irregularly defined. The remaining ones of the plurality of first selected diagnostic characteristics $d_{1,1}$–$d_{1,9}$ are similarly represented so that there are nine different combinations for a skin lesion having certain border and diameter appearance characteristics, as shown in FIG. 2.

As also shown, first panel member 20 includes a viewing window associated with each of the plurality of first selected diagnostics characteristics $d_{1,1}$–$d_{1,9}$ so that there is a first viewing window $w_1$ associated with diagnostic characteristic $d_{1,1}$, a second viewing window $w_2$ associated with diagnostic characteristic $d_{1,2}$ and so on.

Viewing windows $w_1$–$w_9$ are centered about imaginary radial lines $r_1$–$r_9$, respectively, which pass through first central reference point $p_1$. Viewing windows $w_1$–$w_9$ may be formed as apertures through first panel member 20. Alternatively, they may be formed from a transparent material, such as cellophane or the like, to permit a user to discern something therethrough. As shown in FIG. 2, at least some of these viewing windows $w_1$–$w_9$ are positioned at a common radial distance from first central reference point "p1". For example, it may be seen that viewing windows $w_2$ and $w_4$ are positioned at a common radial distance $r_i$ from first central reference point p1, viewing windows $w_3$ and $w_7$ are positioned at a common radial distance $r_{ii}$ from point p1 and viewing windows $w_6$ and $w_8$ are positioned at a common radial distance $r_{iii}$ from point p1. The benefit of having some of these viewing windows located at a common radial distance from first central reference point p1 helps to reduce both the size and the manufacturing costs associated with reference device 10.

A plurality of viewing apertures $v_1$–$v_9$ are also formed through and circumferentially distributed about first panel member 20 so that a viewing aperture is associated with each of the first selected diagnostic characteristics $d_{1,1}$–$d_{1,9}$. These viewing apertures $v_1$–$v_9$ are positioned proximate a peripheral edge 26 of first panel member 20 and constructed similarly to viewing windows $w_1$–$w_9$.

Second panel member 50 may be seen with reference to FIG. 3 wherein second panel member 50 has a second panel member surface 49 which is delineated into a plurality of pie-shaped sectors 51–59. Similarly to first panel member 20, second panel member 50 includes a plurality of second selected diagnostics characteristics of the physical condition, $d_{2,1}$–$d_{2,9}$, distributed thereon in a second array 62 which is defined in that adjacent ones of the second selected diagnostic characteristics $d_{2,1}$–$d_{2,9}$ are spaced apart relative to a second reference point $p_2$ on second panel member surface 49. These second selected diagnostic characteristics of the physical condition $d_{2,1}$–$d_{2,9}$ correspond to a second combination of appearance characteristics of a given skin lesion, namely, the lesion's asymmetry and color. Accordingly, the second selected diagnostic characteristics are pictorially depicted on second panel member surface 49, and indelibly marked thereon, as skin lesions which possess different attributes of these two appearance characteristics. It may be seen that the asymmetry appearance characteristic ranges from no asymmetry, to moderate asymmetry, to high asymmetry. Similarly, the color appearance characteristic ranges from homogeneous, to varied, to highly varied. Accordingly, there are 9 such combinations of these two appearance characteristics for a given skin lesion. For example, and as may be seen with reference to sector 51, second selected diagnostic characteristic $d_{2,1}$ corresponds to a skin lesion having no asymmetry and a homogeneous color. Similarly, as may be seen in sector 59, second selected diagnostic characteristic $d_{2,9}$ corresponds to a skin lesion having a high asymmetry and a highly varied color.

Also indelibly marked on surface 49 a plurality of prognosis indicators 60 associated with each of the second selected diagnostic characteristics $d_{2,1}$–$d_{2,9}$. For each given second selected diagnostic characteristic $d_{2,1}$–$d_{2,9}$ there are two sets of prognosis indicators 60. Accordingly, there is a first set of prognosis indicators 61–69 respectively associated with second selected diagnostic characteristics $d_{2,1}$–$d_{2,9}$ and a second set of prognosis indicators 61'–69' respectively associated with diagnostic characteristics $d_{2,1}$–$d_{2,9}$. Each of the first and second sets of prognosis indicators 61–69 and 61'–69' are arranged in a matrix that is defined by a plurality of radially aligned columns and a plurality of arcuate rows. The plurality of prognosis indicators 60 are shaded any one of four different shades or colors corresponding to a low risk, moderate risk, high risk or very high risk of a skin lesion being melanoma. These risk indicators are graphically depicted in a reference table 70 marked on first panel member surface 24. As also seen in FIG. 3, the first set of prognosis indicator 61–69 in each of sectors 51–59 are identified by a "yes" box which corresponds to an enlarging growth condition of the skin lesion possessing certain diagnostic characteristics, and each of the second set of prognosis indicators 61'–69' within sectors 51–59 is identified by a "no" box corresponding to a stagnant growth condition of a given skin lesion which possesses the specific second combination of second selected diagnostic characteristics $d_{2,1}$–$d_{2,9}$.

Figure 4A:
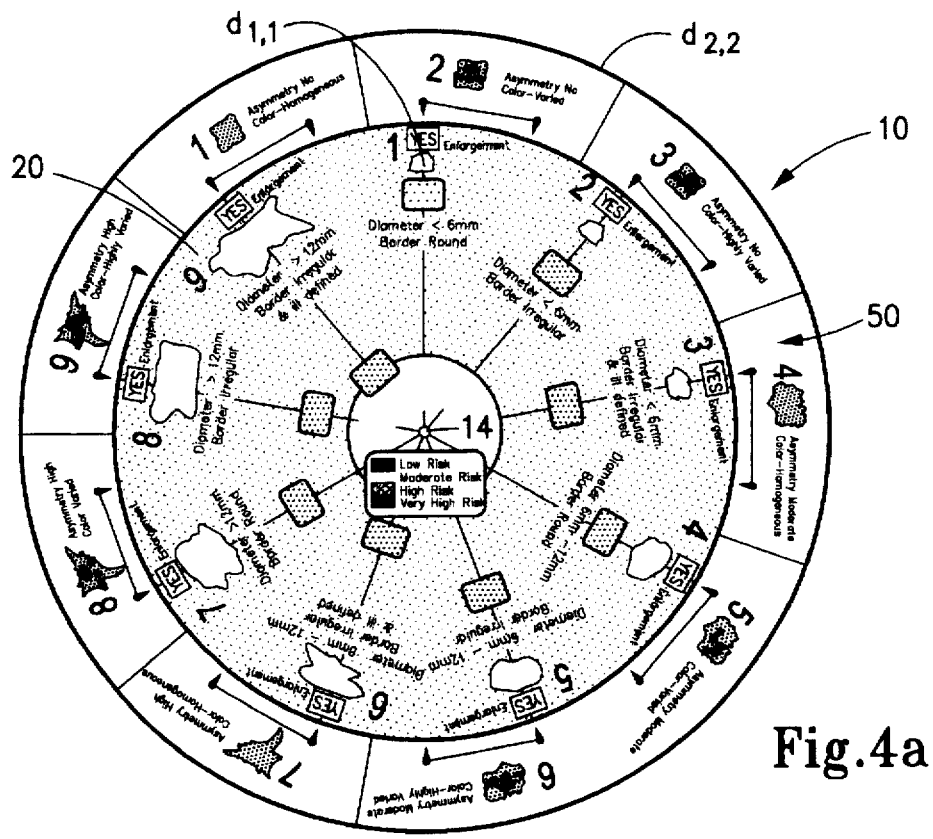
FIG. 4(a) is a top plan view of the reference device according to the first exemplary embodiment of the present invention with the first and second panel members thereof registered to reveal a determinable prognosis indicator associated with a specific combination of diagnostic characteristics of a stagnant physical condition.
Figure 4B:
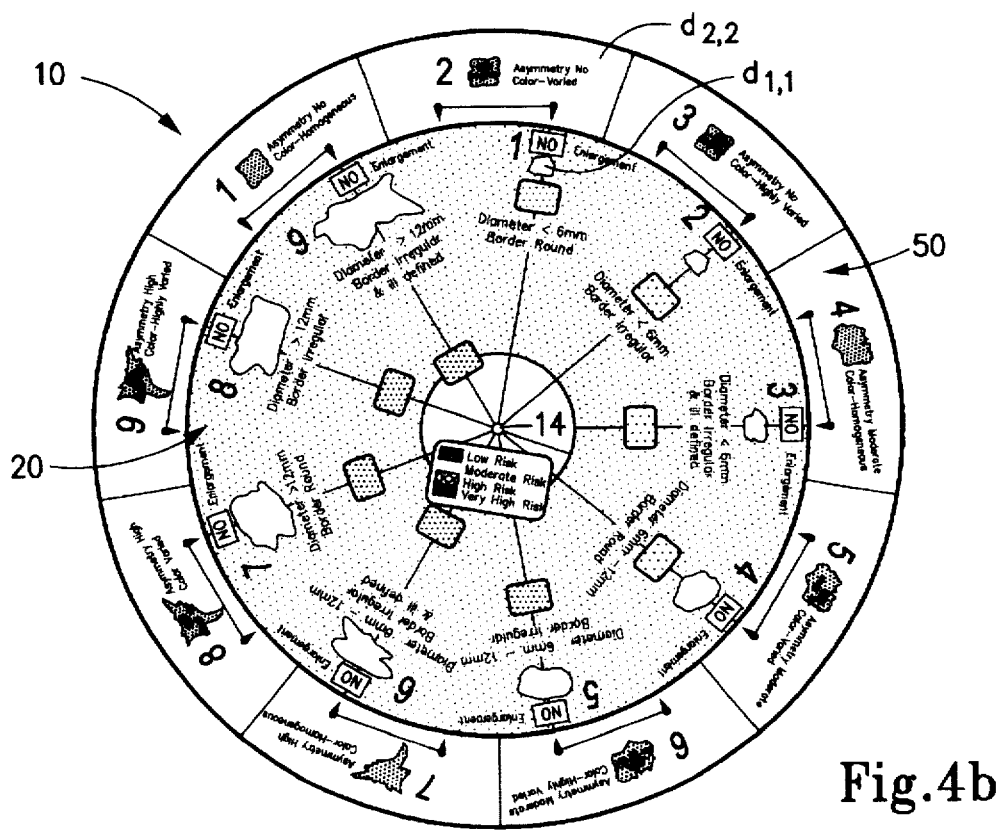
FIG. 4(b) is a top plan view of the reference device according to the first exemplary embodiment of the present invention with the first and second panel members thereof registered to reveal a determinable prognosis indicator associated with a specific combination of diagnostic characteristics of an enlarging physical condition.

With the foregoing discussion in mind in relation to the construction for the first exemplary embodiment of the reference device 10 of the present invention, the operation of the device for indicating prognosis of a physical condition may be best be appreciated now with reference to FIGS. 4(a) and 4(b). The first and second panel members 20, 50 are mounted for relative movement, via a fastener 14 or other appropriate mounting member, whereby a selected one of the first selected diagnostic characteristics $d_{1,1}$–$d_{1,9}$ may be paired with a selected one of the second selected diagnostic characteristics $d_{2,1}$–$d_{2,9}$ to define a specific combination of diagnostic characteristics so that the viewing window associated with the selected one of the first selected diagnostic characteristics $d_{1,1}$–$d_{2,9}$ automatically registers with one of the plurality of prognosis indicators 60 associated with the selected one of the second selected diagnostic characteristics $d_{2,1}$–$d_{2,9}$ thereby to reveal a determinable prognosis indicator corresponding to the specific combination of diagnostic characteristics. To illustrate this operation, FIGS. 4(a) and 4(b) respectively depict how prognosis for a given skin lesion may be indicated where the skin lesion is either enlarging in growth or stagnant in growth. In use, then, either a patient or a doctor may observe a given skin lesion to determine which of the first selected diagnostic characteristics $d_{1,1}$–$d_{1,9}$ and second selected diagnostic characteristics $d_{2,1}$–$d_{2,9}$ exist. This can easily be done by measuring the diameter of the skin lesion and observing its border or outline, the consistency or variation of its color and its asymmetry. A skin lesion with high asymmetry would have approximately one-half of its area being a different color than the other half. Once these characteristics are known, and the user is aware of whether the skin lesion has been enlarging in growth or stagnant, a reliable prognosis of whether the skin lesion is cancerous may be determined.

For example, and with initial reference to FIG. 4(a), it may be seen that the prognosis for an enlarging skin lesion having first selected diagnostic characteristics $d_{1,1}$ (a round border and a diameter of less than 6 mm) and second selected diagnostic characteristics $d_{2,1}$ (no asymmetry and color varied) is high that the skin lesion is cancerous or melanoma. However, and as may be seen in FIG. 4(b), a stagnant skin lesion having these same diagnostic characteristics, $d_{1,1}$ and $d_{2,1}$ has only a moderate risk of being cancerous. It should be appreciated by the ordinarily skilled artisan that a prognosis determination can similarly be made for any one of the numerous remaining combinations of first and second selected diagnostic characteristics and growth characteristics of a given skin lesion, of which there are 162 total such combinations.

As discussed hereinabove, the viewing windows $w_1$–$w_9$ are located at a selected radial distance from the second reference point p2 so that, as the first and second panel members 20, 50 are rotated relative to one another, these viewing windows $w_1$–$w_9$ are positioned to sequentially pass over a row of prognosis indicators that is distributed at the selected radial distance from second reference point p2. Thus, each of the arcuate rows in the matrix of prognosis indicators 60 on second panel member surface 49 is directly correlated to a specific first combination of first selected diagnostic characteristics $d_{1,1}$–$d_{1,9}$. As the knowledgeable medical practitioner would readily understand, the prognosis for some of the first selected diagnostic characteristics of asymmetry and color of a skin lesion is the same irrespective of the combination of second selected diagnostic characteristics $d_{2,1}$–$d_{2,9}$ which the skin lesion possesses. Thus, the prognosis for a skin lesion having first selected diagnostic characteristics $d_{1,2}$ and $d_{1,4}$ is the same and therefore the viewing windows $w_1$ and $w_4$ which are, respectively, associated with these first selected diagnostic characteristics are positioned at a common radial distance from first reference point p1. The same holds true for first selected diagnostic characteristics $d_{1,3}$ and $d_{1,7}$ as well as diagnostic characteristics $d_{1,6}$ and $d_{1,8}$. It should readily understood, then, that the matrix of prognosis indicators 60 need only have six (6) distinct arcuate rows as opposed to nine (9). Of course, the reference device 10 of the present invention could easily be constructed to have nine (9) such arcuate rows, but for cost considerations six (6) rows are preferred. Moreover, it is preferred that first panel member 20 has a diameter which is smaller than the diameter of second panel member 50 as shown in FIGS. 1–4. However, other constructions are certainly contemplated. For example, first panel member 20 could have the same diameter as second panel member 50, yet include a transparent peripheral margin so that the second selected diagnostic characteristics $d_{2,1}$–$d_{2,9}$ could be readily discerned therethrough during alignment.

Figure 5:
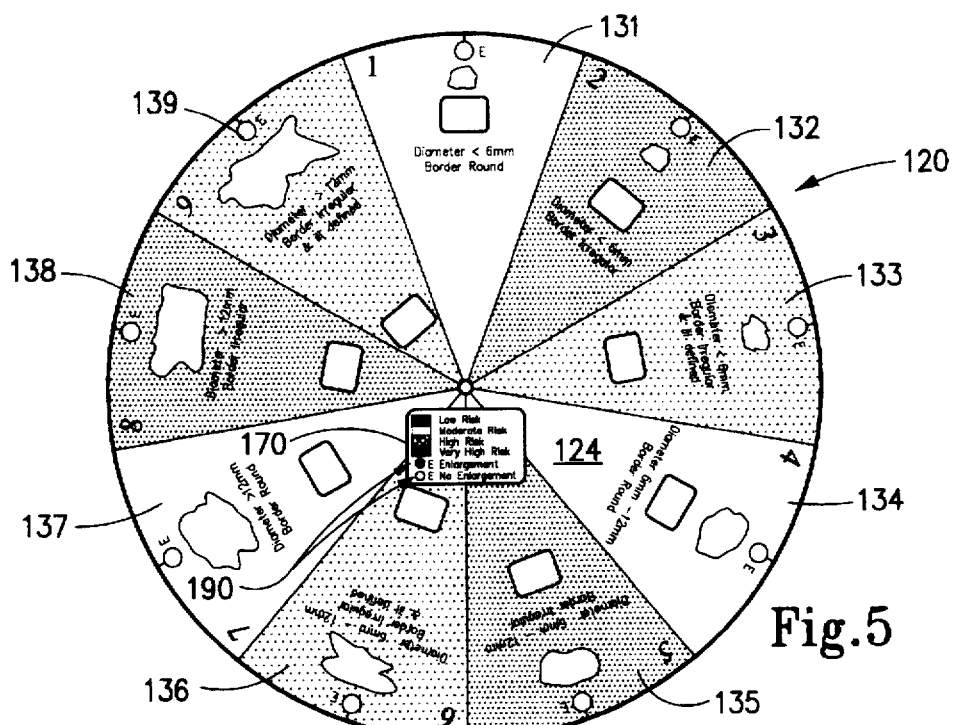
FIG. 5 is a top plan view showing an alterative construction for the first panel member according to a second exemplary embodiment of the present invention.
Figure 6:
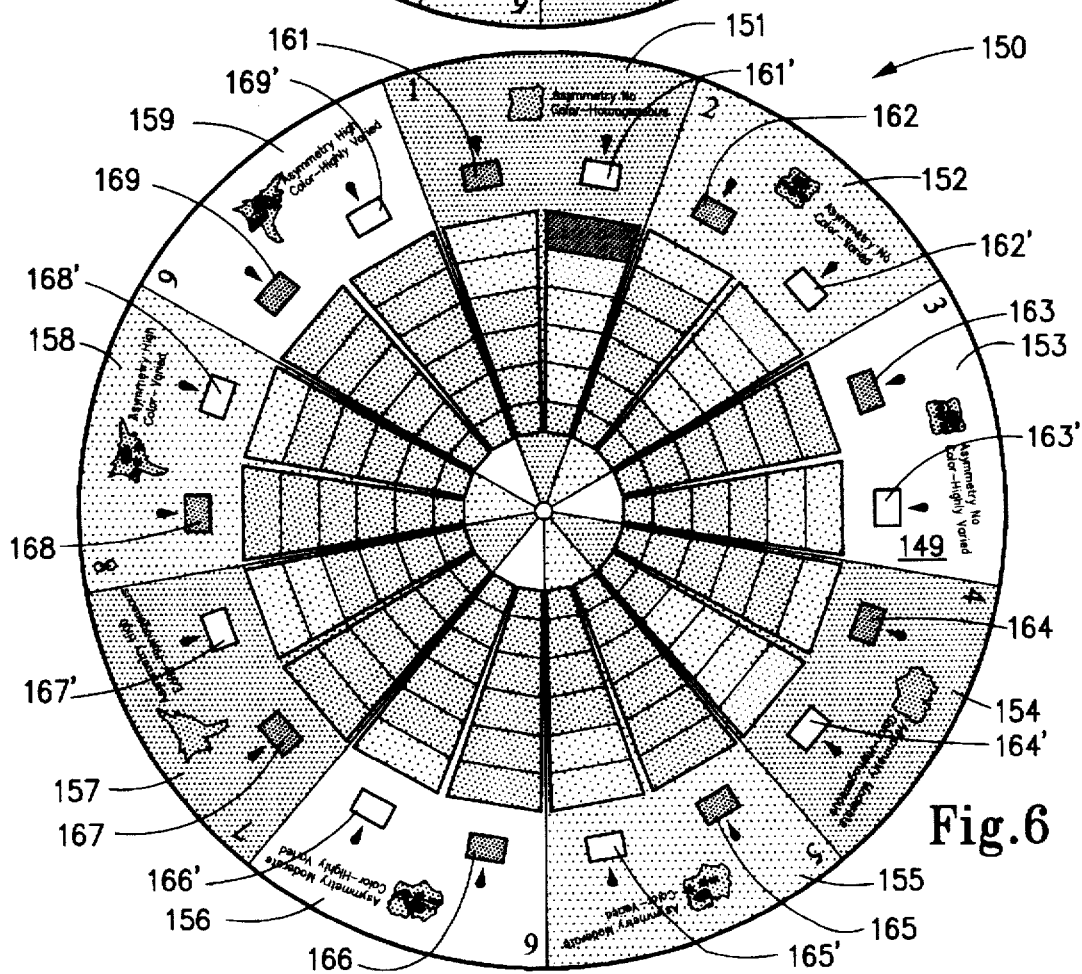
FIG. 6 is a top plan view showing an alternative construction for the second panel member according to the second exemplary embodiment of the present invention.
Figure 7:
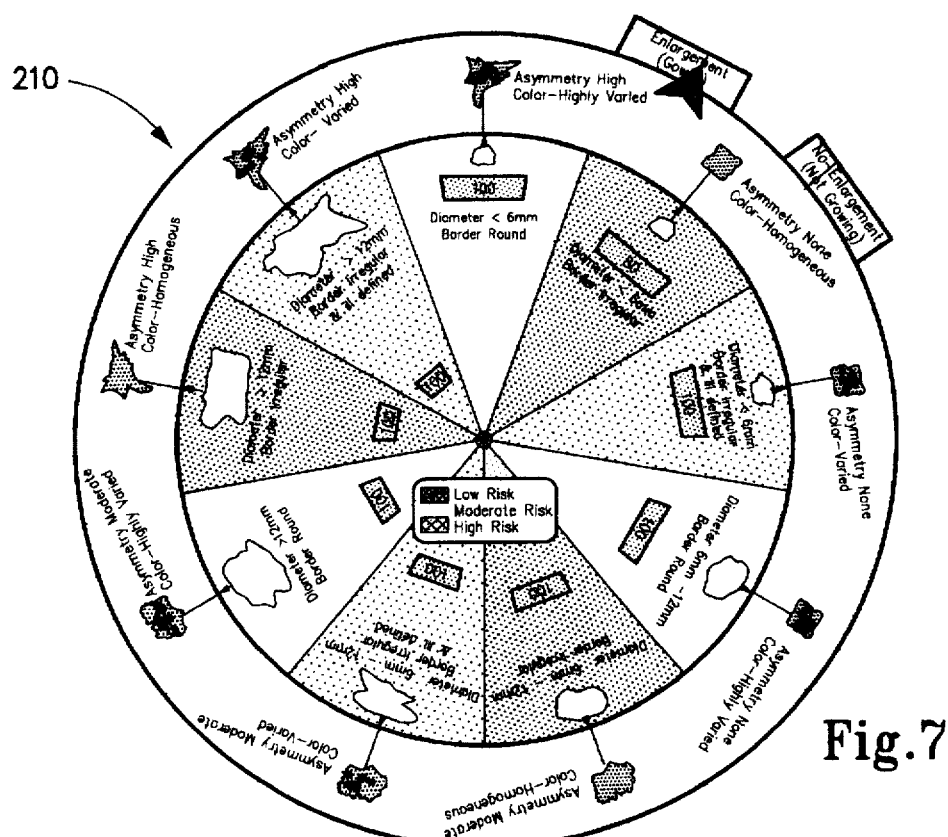
FIG. 7 is a top plan view showing a third exemplary embodiment of the reference device according to the present invention.
Figure 8:
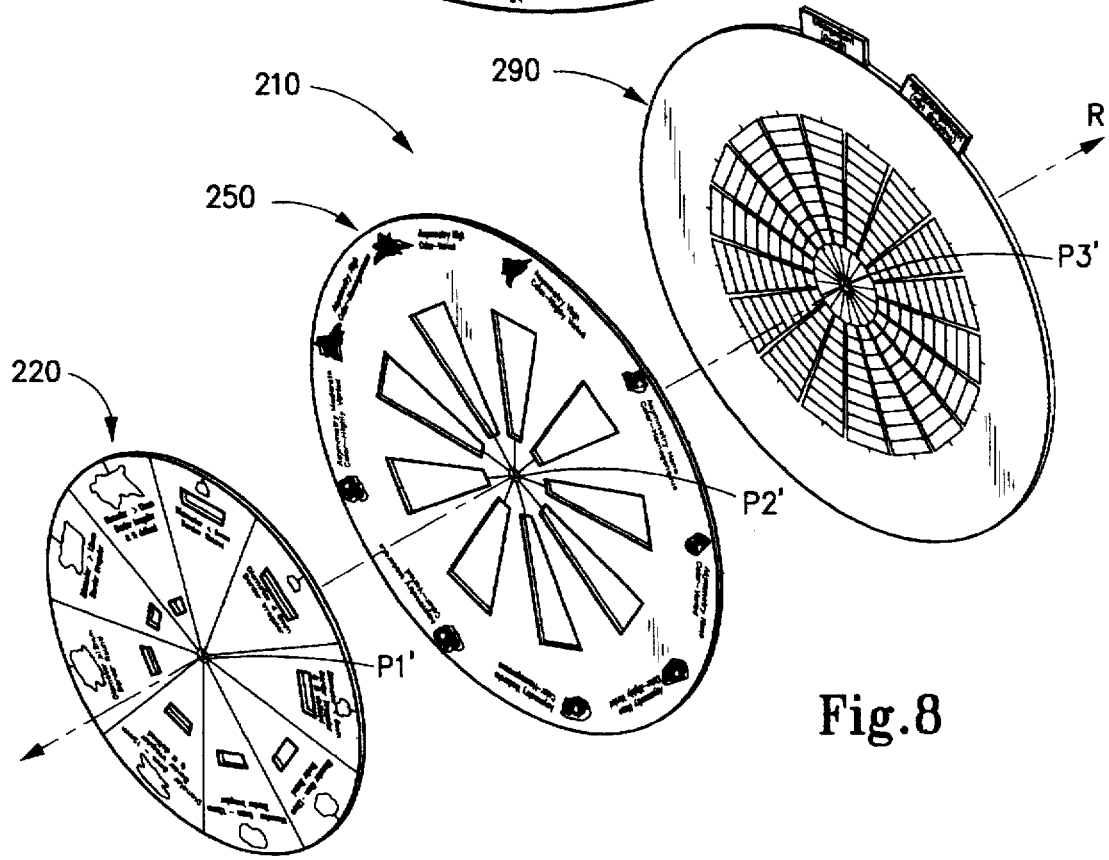
FIG. 8 is an exploded and reduced perspective view showing the construction for the reference device depicted in FIG. 7.

A second exemplary embodiment for the reference device of the present invention is shown now with reference to FIGS. 5 and 6. This second exemplary embodiment of the reference device is constructed similarly to reference device 10 discussed above and operates identically as reference device 10, with the exception that the first and second panel members are marked somewhat differently. As shown in FIG. 5, the first panel member surface 124 of first panel member 120 is delineated into a plurality of pie-shaped zones 131–139, with adjacent ones of these zones 131–139 shaded differently in order to emphasize their presence and orientation on first panel member surface 124. The same is true for second panel member 150 which has shaded zones 151–159.

The second panel member surface 149 of second panel member 150 also has a slightly different appearance in that the rectangular boxes 161–169 corresponding to an enlarging growth of the physical condition and the rectangular boxes 161'–169' corresponding to a stagnation of the physical condition are shaded differently, as opposed to being demarked with "yes" and "no", respectively, as discussed above with reference to FIG. 3. A user is readily able to ascertain that the first set of prognosis indicators 161–169 corresponds to an enlarging growth condition and that the second set of prognosis indicators 161'–169' corresponds to stagnant or non-enlarging growth condition by reference to the enlargement indicators 190 found in reference chart 170 on first panel member surface 124. Apart from these slight differences in appearance of the first and second panel members 120, 150 of the second exemplary embodiment of the reference device, it is virtually identical to reference device 10 discussed previously.

It should be appreciated that a variety of different appearances for the first and second panel members of the reference device of any of the embodiments of the present invention discussed herein can be selected without departing from the scope of the present invention.

Figure 9:
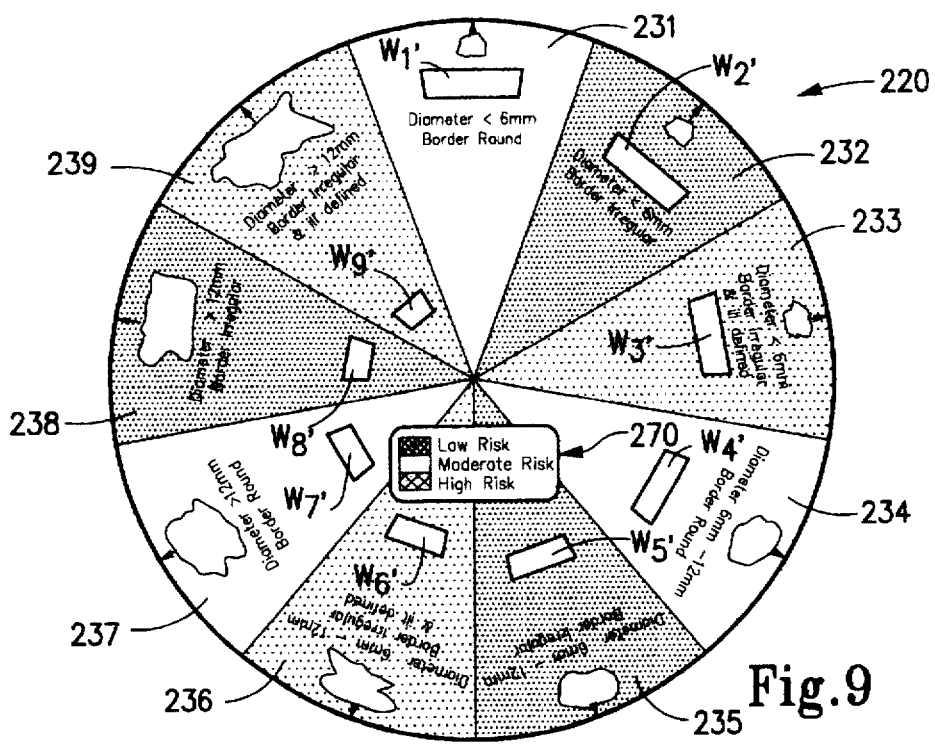
FIG. 9 is a top plan view showing the construction of the first (top) panel member which comprises a component part of the reference device according to the third exemplary embodiment of the present invention.

A third exemplary embodiment of the reference device of the present invention may be seen now with reference to FIGS. 7–11. Here, reference device 210 is shown to have three separate panel members, a first, or top, panel member 220, a second, or middle, panel member 250 and a third, or bottom, panel member 290. Each of these panel members 220, 250 and 290 are mounted for relative movement with one another about an axis of rotation "R" passing through their central reference points p1', p2' and p3'. First panel member 220 is shown in FIG. 9 wherein it may be seen that this first panel member 220 is constructed similarly as above, with a few notable exceptions. First, the viewing windows $w_1'$–$w_9'$ are each differently sized, although this is not necessary as will be appreciated.

Figure 10:
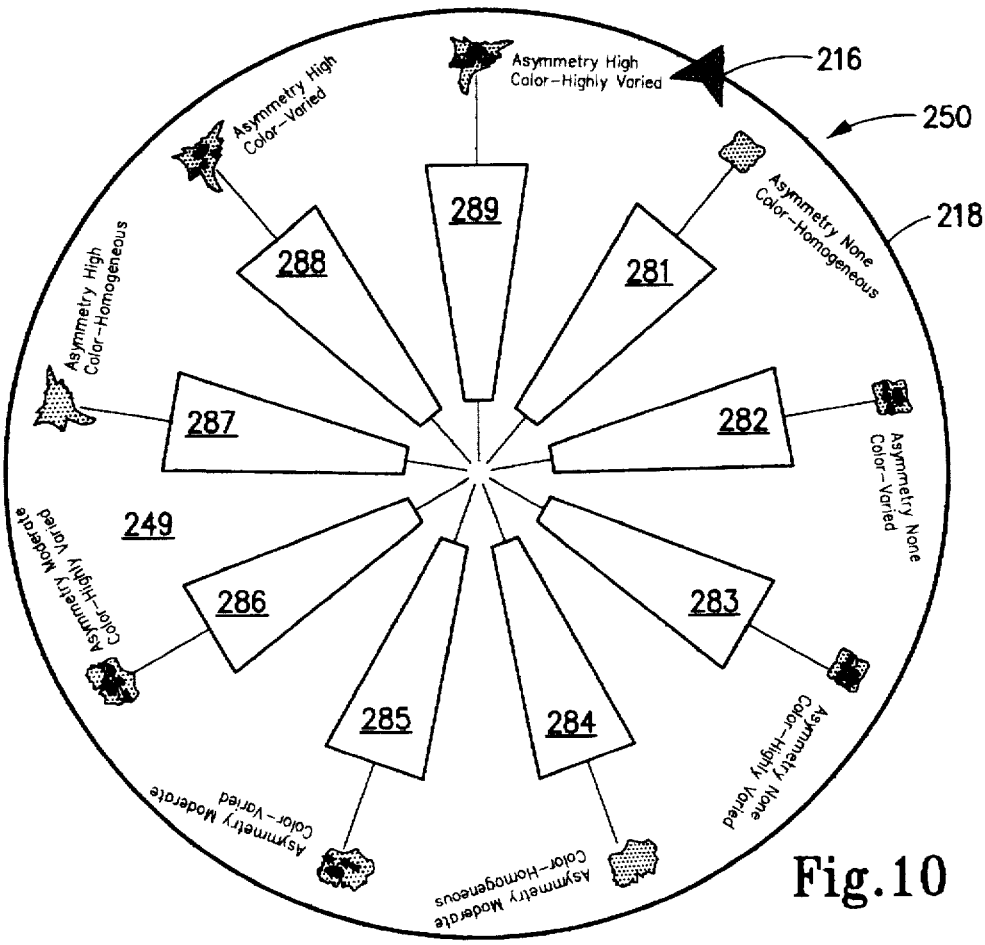
FIG. 10 is a top plan view showing the construction of the second (middle) panel member which comprises a component part of the reference device according to the third exemplary embodiment of the present invention.
Figure 11:
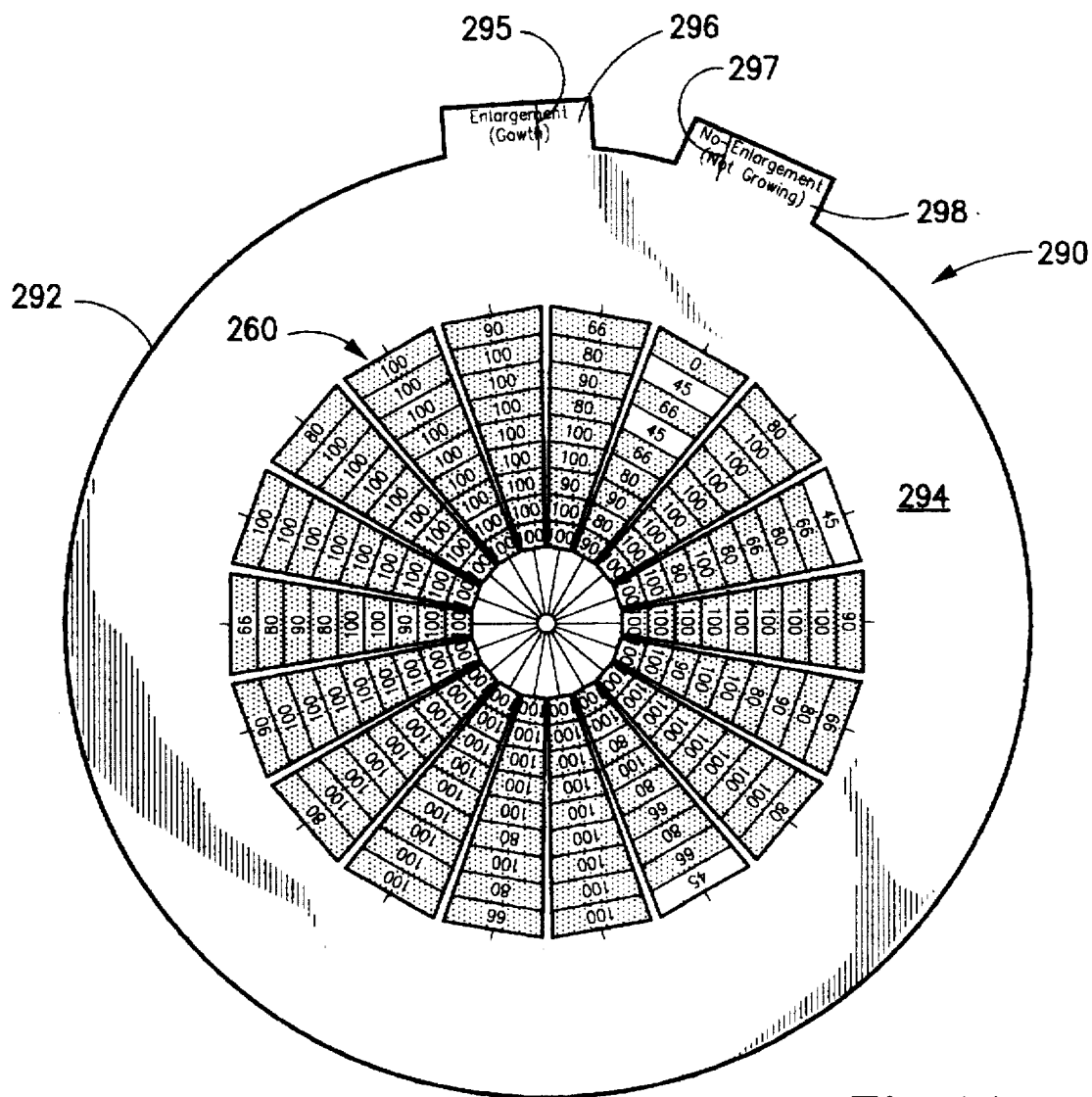
FIG. 11 is a top plan view showing the construction of the third (bottom) panel member which comprises a component part of the reference device according to the third exemplary embodiment of the present invention.

With this embodiment, however, the first panel member surface 224 is not provided with viewing apertures associated with each of sectors 231–239 as was discussed above with reference to FIG. 2. Moreover, the reference table 270 on first panel member surface 224 is only provided with three different risk indicators as opposed to the four different risk indicators that have been discussed previously with reference to the first and second embodiments. It may be seen that the "very high risk" indicator is not used in this embodiment. In all other respects, first panel member 120 is substantially identical to first panel member 220 discussed above with reference to the second exemplary embodiment of the present invention. That is, adjacent ones of its sectors 231–239 are shaded differently thereby to emphasize their presence and orientation, as well as other similar features. As shown in FIG. 10, second panel member 250 is constructed noticeably differently than discussed above. While second panel member 250 still has pictorial representations of the second selected diagnostic characteristics $d_{2,1}$–$d_{2,9}$ indelibly marked thereon, it is not provided with the matrix of prognosis indicators. Instead, second panel member 250 has a plurality of enlarged trapezoidal-shaped openings 281–289 formed therethrough, with there being one such opening associated with each of the second selected diagnostic characteristics $d_{2,9}$–$d_{2,9}$. In addition, a pointing arrow 216 is provided and extends from a peripheral edge 218 of second panel member 250.

Instead, third panel member 290, which is configured generally as a dial having the same diameter as second panel member 250, is provided with the matrix of prognosis indicators 260. This matrix is similar to that discussed previously in that it is comprised of a plurality of radially aligned columns and a plurality of arcuate rows. Each of the prognosis indicators 260 in each of the arcuate rows is positioned at a common radial distance from the third reference point p3' on third panel member surface 294. A pair of spaced apart alignment tabs 296 and 298 protrude radially outwardly from a peripheral edge 292 of third panel member 290 and each of these tabs is provided with a positioning line 295 and 297, respectively. As may be seen, tab 296 corresponds to an enlarging growth condition of a skin lesion, while tab 298 corresponds to stagnation of the skin lesion.

Figure 12A:
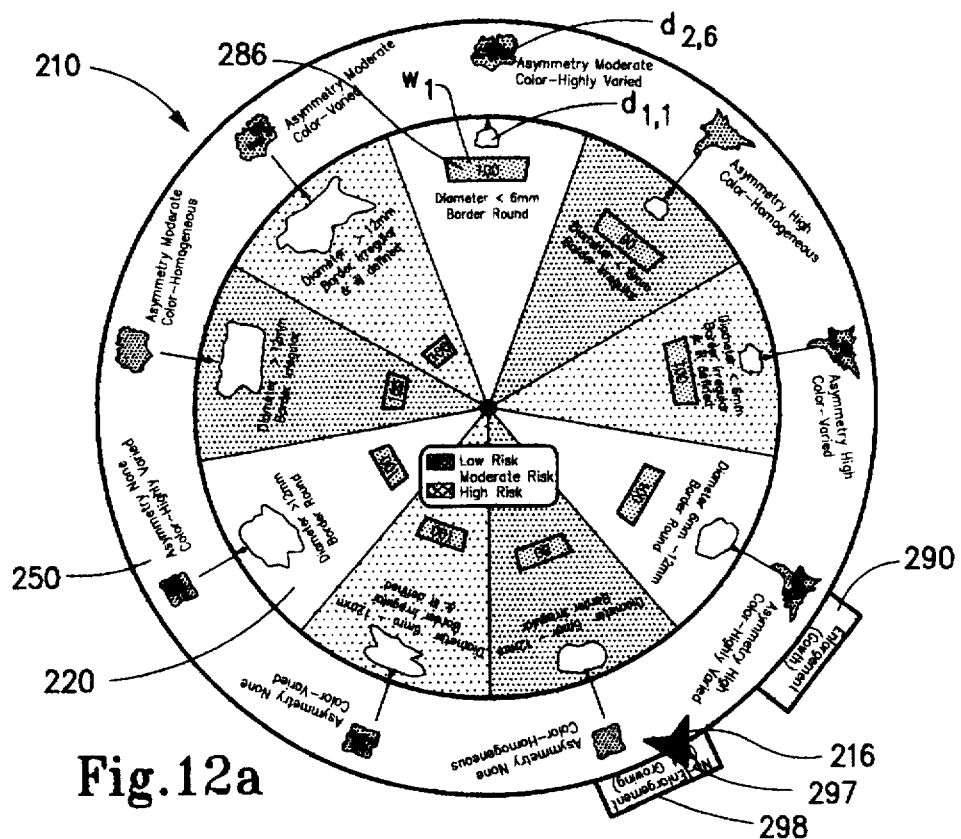
FIG. 12($a$) is a reduced top plan view of the reference device according to the third exemplary embodiment of the present invention with the first, second and third panel members thereof registered to reveal a determinable prognosis indicator associated with a specific combination of diagnostic characteristics of stagnant physical condition.
Figure 12B:
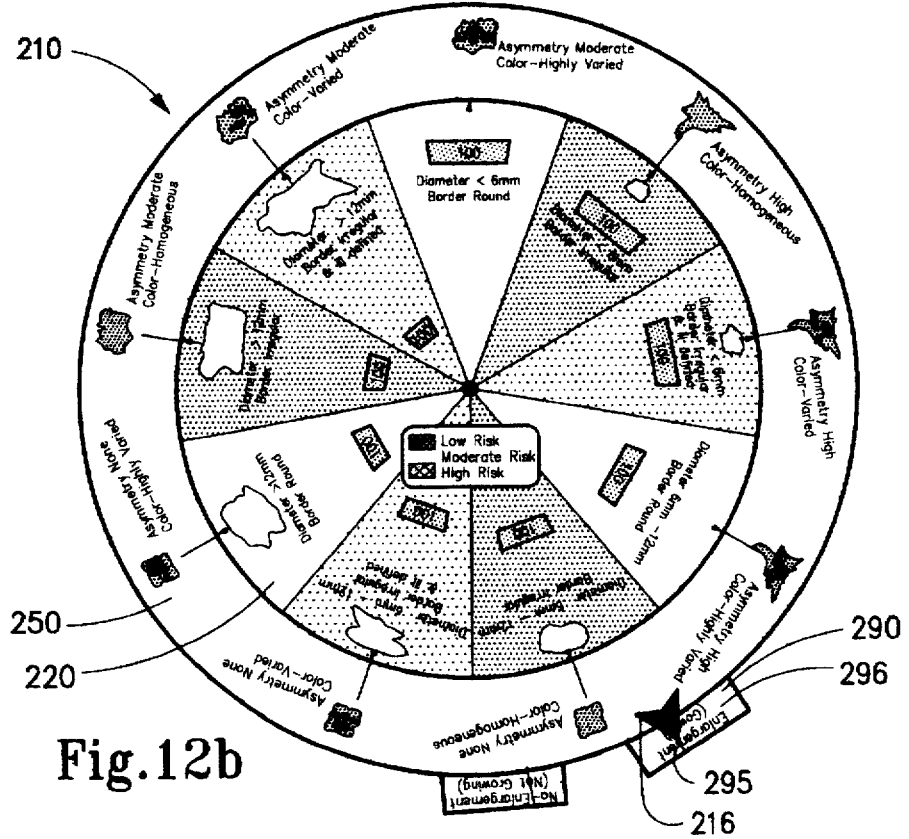

The operation of this third exemplary embodiment of the reference device 210 of the present invention may be now appreciated with reference to FIGS. 12(a) and 12(b). Once a patient or a doctor has assessed the specific characteristics of a given skin lesion based on its asymmetry, color, diameter and border, then the first and second panel members 220, 250 may be rotated relative to one another whereby selected ones of the first and second selected diagnostic characteristics $d_{1,1}$–$d_{1,9}$ and $d_{2,1}$–$d_{2,9}$ can be paired to define a specific combination of diagnostic characteristics. When so paired, a selected one of the viewing windows $w_1$–$w_9$ associated with first panel member 220 automatically registers with a selected one of the openings 281–289 formed through second panel member 250. Thereafter, third panel member 290 may be rotated so that one of the prognosis indicators 260 may be viewed through both the selected viewing window and the selected opening thereby to reveal a determinable prognosis indicator corresponding to the specific combination of diagnostic characteristics.

To illustrate, FIG. 12(a) shows how a prognosis for a growing skin lesion may be determined based upon the lesion's particular diagnostics characteristics. In FIG. 12(a), the first and second panel members 220, 250 are rotated whereby a first selected diagnostic characteristic $d_{1,1}$ (corresponding to a skin lesion having a round border and a diameter less than 6 mm) is paired with a second selected diagnostic characteristic $d_{2,6}$ (corresponding to the same skin lesion having moderate asymmetry and highly varied color). First and second panel members 220, 250 are then retained in this orientation and third panel member 290 is rotated so that pointer tab 216 aligns with positioning line 297 of tab 298. It may then be determined by a user, by viewing through the combination of both viewing window $w_1$ and opening 286, that there is a high risk that the skin lesion having this particular combination of selected diagnostic characteristics is cancerous. Similarly, and with reference now to FIG. 12(b), it may be seen that when pointer tab 216 is aligned with positioning line 295 associated with tab 296 there is also a high risk that the skin lesion is cancerous, even if it is growing.

Figure 13:
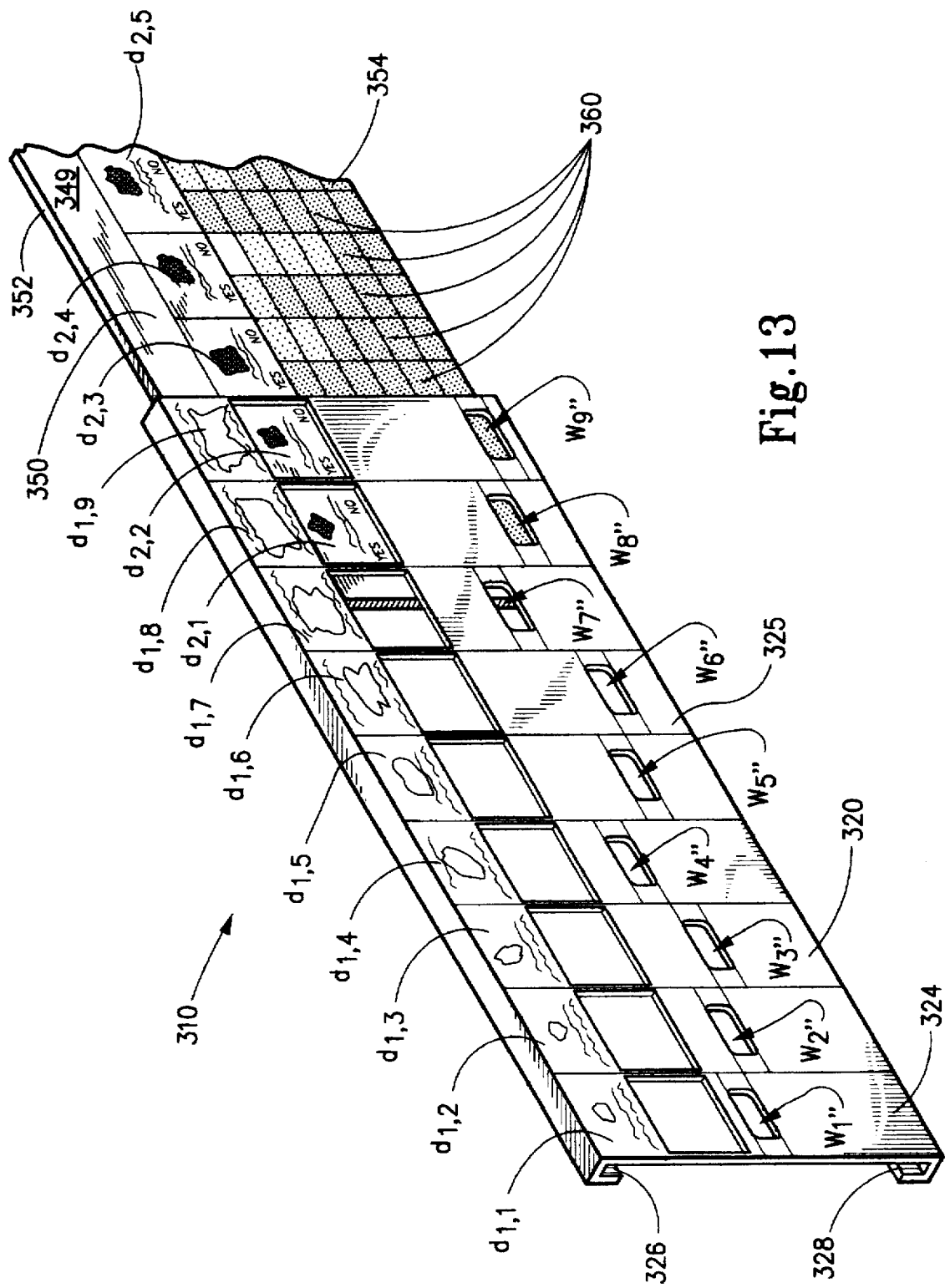
FIG. 13 is a perspective view broken away depicting a fourth exemplary embodiment of the reference device according to the present invention.

Finally, FIG. 13 depicts a fourth exemplary embodiment of the reference device according to the present invention. In reference device 310, first panel member 320 is shown to be slidable relative to second panel member 350 to reveal a determinable prognosis indicator corresponding to a specific combination of diagnostic characteristics of the physical condition. Here, adjacent ones of the plurality of first selected diagnostic characteristics $d_{1,1}$–$d_{1,9}$ are spaced apart equidistantly on first panel member surface 324. A transparent viewing window $w_1''$–$w_9''$ is respectively associated with each of the first selected diagnostic characteristics $d_{1,1}$–$d_{1,9}$, and these viewing windows $w_1''$–$w_9''$ are located at appropriate distances from a lower edge 325 of first panel member 320.

Second selected diagnostic characteristics $d_{2,1}$–$d_{2,9}$ are distributed on second panel member surface 349, with adjacent ones of these also equidistantly spaced apart from each other. A vertical column of prognosis indicators 360 is associated with each of the second diagnostic characteristics $d_{2,1}$–$d_{2,9}$. Second panel member 350 includes a pair of elongated rails 352 and 354 which are sized and adapted for slidable engagement with a pair of elongated channels 326 and 328 formed on first panel member 320. As such, it may be appreciated that second panel member 350 may slidably engage panel member 320 whereby a selected one of the first diagnostic characteristics $d_{1,1}$–$d_{1,9}$ may be paired with a selected one of second diagnostic characteristics $d_{2,1}$–$d_{2,9}$ to reveal a determinable prognosis indicator through an associated one of viewing windows $w_1''$–$w_9''$. Of course, it should also be appreciated that the specific construction for the fourth exemplary construction for the reference device 310 should not be unduly confined to that depicted here, as one in the art would readily recognize.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A reference device for indicating prognosis of a physical condition based upon selected diagnostic characteristics of the physical condition, comprising:

(a) a first panel member having a first panel member surface, said first panel member surface including a plurality of first selected diagnostic characteristics of the physical condition distributed thereon in a first array which is defined in that adjacent ones of said first selected diagnostic characteristics are spaced apart relative to one another from a first central reference point on said first panel member surface, said first panel member surface further including a viewing window associated with each of said plurality of first selected diagnostic characteristics; and (b) a second panel member having a second panel member surface which includes a plurality of second selected diagnostic characteristics of the physical condition distributed thereon in a second array which is defined in that adjacent ones of said second selected diagnostic characteristics are spaced apart relative to a second central reference point on said second panel member surface, said second panel member further including a plurality of prognosis indicators associated with each of said second selected diagnostic characteristics, said second panel member mounted for relative movement with said first panel member whereby a selected one of said first selected diagnostic characteristics may be paired with a selected one of said second selected diagnostic characteristics to define a specific combination of diagnostic characteristics so that the viewing window associated with the selected one of said first selected diagnostic characteristics automatically registers with one of the plurality of prognosis indicators associated with the selected one of said second selected diagnostic characteristics, thereby to reveal a determinable prognosis indicator corresponding to the specific combination of diagnostic characteristics.

2. A reference device according to claim 1 wherein said second panel member is slidable relative to said first panel member.

3. A reference device according to claim 1 wherein said second panel member is operative to rotate relative to said first panel member about an axis of rotation passing through said first and second central reference points.

4. A reference device according to claim 3 wherein said first selected diagnostic characteristics are distributed as a circular arrangement about the first central reference point.

5. A reference device according to claim 3 wherein said second selected diagnostic characteristics are distributed as a circular arrangement about the second central reference point.

6. A reference device according to claim 3 wherein each of said first and second panel members is configured as a dial.

7. A reference device according to claim 6 wherein said first panel member has a smaller diameter than said second panel member.

8. A reference device according to claim 6 wherein at least some of said viewing windows are positioned at a common radial distance from the first central reference point.

9. A reference device according to claim 3 wherein said second panel member includes at least a first set of said prognosis indicators associated with each of said plurality of first selected diagnostic characteristics.

10. A reference device according to claim 9 wherein said first sets of prognosis indicators are arranged in a matrix that is defined by a plurality of radially aligned columns and a plurality of arcuate rows, and wherein the prognosis indicators in each of said rows are positioned at a common radial distance from said second central reference point.

11. A reference device according to claim 10 wherein each of said viewing windows is located at a selected radial distance from said second central reference point so that each of said viewing windows is positioned to sequentially pass over a row of prognosis indicators that is distributed at the selected radial distance from the second central reference point.

12. A reference device according to claim 11 wherein at least some of said viewing windows are located at a common radial distance from the second central reference point.

13. A reference device according to claim 10 wherein said matrix is centered about the second central reference point.

14. A reference device according to claim 9 including a second set of prognosis indicators associated with each of said second selected diagnostic characteristics, each of said first set of prognosis indicators corresponding to enlarging growth of the physical condition and each of said second set of prognosis indicators corresponding to stagnant growth of the physical condition.

15. A reference device according to claim 14 wherein said first and second sets of prognosis indicators are arranged in a matrix that is defined by a plurality of radially aligned columns and a plurality of arcuate rows, and wherein the prognosis indicators in each of said rows are positioned at a common radial distance from said second central reference point.

16. A reference device according to claim 15 wherein each of said viewing windows is located at a selected radial distance from the second reference point so that each of said viewing windows is positioned to sequentially pass over a row of prognosis indicators that is distributed at the selected radial distance from the second central reference point.

17. A reference device according to claim 16 wherein at least some of said viewing windows are located at a common radial distance from the second central reference point.

18. A reference device according to claim 15 wherein said matrix is centered about the second central reference point.

19. A reference device according to claim 1 wherein each of said first selected diagnostic characteristics and its associated said viewing window occupies a delineated zone on said first panel member surface, with adjacent ones of said zones shaded differently thereby to emphasize presence and orientation of said zones.

20. A reference device according to claim 1 wherein each said second selected diagnostic characteristics and its associated said prognosis indicators occupies a delineated zone on said second panel member surface, with adjacent ones of said zones shaded differently thereby to emphasize presence and orientation of said zones.

21. A reference device for prognosing melanoma based upon selected diagnostic characteristics of a skin lesion, comprising:
   (a) a first panel member having a first panel member surface, said first panel member surface including a plurality of first selected diagnostic characteristics of the skin lesion indelibly marked thereon in a first array which is defined in that adjacent ones of said first selected diagnostic characteristics are spaced apart relative to one another from a first central reference point on said first panel member surface, said first panel member surface further including a viewing window associated with each of said plurality of first selected diagnostic characteristics; and
   (b) a second panel member having a second panel member surface which includes a plurality of second selected diagnostic characteristics of the skin lesion indelibly marked thereon in a second array which is defined in that adjacent ones of said second selected diagnostic characteristics are spaced apart relative to a second central reference point on said second panel member surface, said second panel member further including a plurality of melanoma prognosis indicators associated with each of said second selected diagnostic characteristics and indelibly marked on said second panel member surface, said second panel member mounted for rotation relative to said first panel member whereby a selected one of said first selected diagnostic characteristics may be paired with a selected one of said second selected diagnostic characteristics to define a specific combination of diagnostic characteristics so that the viewing window associated with the selected one of said first selected diagnostic characteristics automatically registers with one of the plurality of melanoma prognosis indicators associated with the selected one of said second selected diagnostic characteristics, thereby to reveal a determinable melanoma prognosis indicator corresponding to the specific combination of diagnostic characteristics of the skin lesion.

22. A reference device according to claim 21 wherein each of said plurality of first selected diagnostic characteristics of the skin lesion is a first combination of appearance characteristics selected from a group consisting of asymmetry, color, border and diameter of the skin lesion.

23. A reference device according to claim 22 wherein each of said plurality of second diagnostic characteristics of the skin lesion is a second combination of appearance characteristics selected from a group consisting of asymmetry, border, color and diameter of the skin lesion, said second combination different from said first combination.

24. A reference device according to claim 23 wherein said asymmetry is selected from a group consisting of no asymmetry, moderate asymmetry and high asymmetry.

25. A reference device according to claim 23 wherein said border is selected from a group consisting of round, irregular and irregular and ill-defined.

26. A reference device according to claim 23 wherein said color is selected from a group consisting of homogenous, varied and highly varied.

27. A reference device according to claim 23 wherein said diameter is selected from a group consisting of less than six millimeters, between six and twelve millimeters and greater than twelve millimeters.

28. A reference device according to claim 23 wherein said asymmetry is selected from a group consisting of no asymmetry, moderate asymmetry and high asymmetry, said border selected from a group consisting of round, irregular and irregular and ill-defined, said color selected from a group consisting of homogenous, varied and highly varied, and wherein said diameter is selected from a group consisting of less than six millimeters, between six and twelve millimeters and greater than twelve millimeters.

29. A reference device according to claim 21 wherein each of said plurality of melanoma prognosis indicators is selected from a group consisting of low risk, moderate risk, high risk and very high risk.

30. A reference device for indicating prognosis of a physical condition based upon selected diagnostic characteristics of the physical condition, comprising:
   (a) a first panel member having a first panel member surface which includes a plurality of first selected diagnostic characteristics of the physical condition distributed thereon in a first array that is defined in that adjacent ones of said first selected diagnostic characteristics are angularly spaced apart relative to a first central reference point on said first panel member surface, there being a first panel member viewing window associated with each of said plurality of first selected diagnostic characteristics;

(b) a second panel member having a second panel member surface which includes a plurality of second selected diagnostic characteristics of the physical condition distributed thereon in a second array that is defined in that adjacent ones of said second selected diagnostic characteristics are angularly spaced apart relative to a second central reference point on said second panel member surface, there being a second panel member viewing window associated with each of said plurality of second selected diagnostic characteristics; and (c) a third panel member having a third panel member surface which includes a plurality of prognosis indicators distributed thereon in a graphic array relative to a third central reference point on said third panel member surface, said first, second and third panel members mounted for relative movement with one another about an axis of rotation passing through said central reference points whereby selected ones of said first and second selected diagnostic characteristics may be paired to define a specific combination of diagnostic characteristics so that associated ones of said first and second panel member viewing windows register, and whereby said third panel member may thereafter by rotated so that one of said prognosis indicators may be viewed through said first and second viewing windows thereby to reveal a determinable prognosis indicator corresponding to the specific combination of diagnostic characteristics.

* * * * *